United States Patent
Huo et al.

(10) Patent No.: US 8,433,120 B2
(45) Date of Patent: Apr. 30, 2013

(54) METHOD FOR IMAGE PROCESSING OF MAMMOGRAPHIC IMAGES

(75) Inventors: Zhimin Huo, Pittsford, NY (US); Ke Nie, Rochester, NY (US); Jing Zhang, HuangPu District (CN); Fan Xu, Pudong (CN)

(73) Assignee: Carestream Health, Inc., Rochester, NY (US)

( * ) Notice: Subject to any disclaimer, the term of this patent is extended or adjusted under 35 U.S.C. 154(b) by 422 days.

(21) Appl. No.: 12/712,226

(22) Filed: Feb. 25, 2010

(65) Prior Publication Data

US 2011/0206261 A1 Aug. 25, 2011

(51) Int. Cl.
*G06K 9/00* (2006.01)
*G06Q 10/00* (2012.01)

(52) U.S. Cl.
USPC .............................. 382/132; 705/3

(58) Field of Classification Search .............. 382/132
See application file for complete search history.

(56) References Cited

U.S. PATENT DOCUMENTS

| | | | |
|---|---|---|---|
| 5,268,967 A | 12/1993 | Jang et al. | |
| 5,357,549 A | 10/1994 | Maack et al. | |
| 5,633,511 A | 5/1997 | Lee et al. | |
| 5,835,618 A | 11/1998 | Fang | |
| 6,778,691 B1 | 8/2004 | Barski et al. | |
| 7,221,786 B2 | 5/2007 | Luo et al. | |
| 2006/0222223 A1* | 10/2006 | Bi et al. | 382/128 |
| 2007/0269106 A1 | 11/2007 | Huo et al. | |
| 2009/0190716 A1 | 7/2009 | Yang et al. | |
| 2009/0296999 A1* | 12/2009 | Raundahl et al. | 382/128 |
| 2010/0046814 A1* | 2/2010 | Dewaele et al. | 382/128 |

OTHER PUBLICATIONS

Ulrich Bick, et al. "Density Correction of Peripheral Breast Tissue on Digital Mammograms" *RadioGraphics*, Nov. 1996, pp. 1403-1411.
Commonly assigned U.S. Appl. No. 12/482,651, filed Jun. 11, 2009, titled: Rendering for Improved Diagnostic Image Consistency, by Huo et al.
Commonly assigned U.S. Appl. No. 12/471,675, filed May 26, 2009, titled: Assessment of Breast Density and Related Cancer Risk, by Huo et al.

* cited by examiner

*Primary Examiner* — Hiep V Nguyen (57) ABSTRACT

A method for rendering a mammography image. Mammography image data is obtained and stored in a computer-readable electronic memory. A mapping transforms the data to an output data space by estimating a relative amount of dense tissue from the image data; identifying at least a first control point that delineates tissue from non-tissue image content and a second control point that delineates a fatty from a dense tissue region; allocating output image data values in the output data space for the identified fatty and dense tissue content according to the estimated relative amount of dense tissue; and mapping image data values to the allocated output image data values according to the first and second control points. The mammography image is rendered on a display according to the mapping.

20 Claims, 11 Drawing Sheets

METHOD FOR IMAGE PROCESSING OF MAMMOGRAPHIC IMAGES

FIELD OF THE INVENTION

This invention generally relates to processing of radiographic images for mammography and more particularly relates to a method for consistent rendering for mammography.

BACKGROUND OF THE INVENTION

Consistency in image rendering helps to allow a more accurate clinical evaluation when using x-rays and related types of diagnostic images. Images taken of the same anatomy that have the same overall dynamic range and contrast settings can be more readily compared against one another for diagnosis and for tracking various conditions, particularly for images taken of the same patient at different times and on different imaging apparatus.

However, due to differences in variables such as equipment used, techniques applied, and image pre-processing, consistent rendering of radiographic images can be difficult to achieve. Thus, even for images obtained from the same patient over a short treatment interval, there can be differences between two or more images that prevent effective comparison between them and constrain the ability of the clinician to detect subtle changes that can be highly significant. This problem relates to images whether originally obtained on film and scanned, or digitally obtained, such as using a computed radiography (CR) or digital radiography (DR) system. Some progress has been made with different types of x-rays, particularly for chest x-ray and related imaging. In practice, however, consistent image rendering has generally proved difficult to achieve.

For a number of reasons, providing consistent rendering for mammography images is acknowledged to be particularly challenging. Mammography is characterized by low power levels relative to other radiography methods and by the need to pre-process the image data that is obtained from the low-level exposure properly so that subtle changes in soft tissue can be more clearly discerned. The breast is a non-rigid 3D structure and breast compression is required for a better image quality. Both the positioning of the breast and the level of compression used can be substantially varied from one acquisition to the next. Variations in imaging techniques, compression, positioning, and image processing techniques tend to result in significant differences in image appearance and quality. Due in part to these factors and to the overall complexity of the problem, consistent rendering has not been given considerable attention for mammography imaging processing. Because of this, radiologists are often required to adapt to system-related rendering differences, even for images related to the same patient, but taken at different times.

The average breast generally has about 50% fibroglandular tissue, a mixture of fibrous connective tissue and the glandular epithelial cells that line the ducts of the breast (the parenchyma), and 50% fat tissue. However, the radiological appearance of the breast varies between individuals, in part, because of variations in the relative amounts of fatty and dense fibroglandular tissue. As a guideline for classification, the American College of Radiology (ACR) Breast Imaging Reporting and Data System (BIRADS) has identified four major groupings for breast tissue density. Class I corresponds to breasts having high concentration of fat tissue. The Class II grouping indicates scattered fibroglandular densities. Class III indicates heterogeneously dense tissue. Class IV corresponds to extremely high breast density.

A particular problem for mammography evaluation relates to similar densities between different tissue types and similar density between cancer lesions and fibroglandular tissue, usually termed dense tissue. Women with increased mammographic parenchymal density can have four- to six times the cancer risk of women with primarily fatty breasts. Since most breast cancers develop from the epithelial cells that line the ducts of the breast, having more of this tissue, as reflected by increased mammographic density, may indicate higher likelihood of developing breast cancer. Studies have found that lesions in higher density areas are themselves more difficult to detect from the mammogram than are lesions in fatty regions, somewhat compounding the problem. The challenge on rendering of mammographic images is to properly enhance the contrast for the viewer, to better differentiate or magnify subtle differences between breast tissues and between cancers and normal breast tissues in density.

Comparison of current mammograms with prior exams has been one of the common approaches used to detect changes over time as a sign of early cancer. Because of this practice, image consistency has a role in diagnosis of breast cancer using mammography. However, image consistency rendering for mammography remains a challenge as a result of these factors.

As discussed earlier, the amount of dense tissue can vary significantly from one individual to another. While increased breast density is associated with an increased risk of breast cancer, the amount of dense tissue also decreases as age increases. Responding properly to the variation in the amount of dense tissue from one individual to another and to this variation for the same individual from one exam to another represents considerable challenge for consistency rendering in mammography, in light of the factors that govern consistency rendering in mammographic images.

Breast density, sometimes expressed as mammographic percent density, or MPD, can be calculated to help clinicians in categorizing the breast tissues into Classes I-IV described above. An approach is proposed to estimate the MPD by Huo et al. in commonly assigned U.S. Ser. No. 12/471,675 filed May 26, 2009, entitled "Assessment of Breast Density and Related Cancer Risk". Since fat has a lower effective atomic number than that of fibroglandular tissue, there is less x-ray attenuation from fatty tissue than from denser fibroglandular tissue. Fat appears dark (that is, has a higher optical density) on a mammogram, while fibroglandular tissue appears light (that is, exhibits a lower optical density). Regions of brightness associated with fibroglandular tissue are normally considered by diagnosticians to have increased "mammographic density". Information on breast density or MPD can help clinicians to better manage patient care and cancer risk. Use of this information in image processing could potentially help to render images consistently. Tone-scale adjustment based on the amount of dense tissue in the image as a reference will allow consistent rendering of mammographic images among patients and across different imaging modality and image processing. In addition, one can manage the rendering of dense tissue portions so that cancers can be better enhanced in dense tissue.

Computed radiography systems that use storage phosphors and digital radiography systems can offer a very wide exposure latitude (as much as 10,000:1) compared with that available from conventional screen/film systems (typically 40:1). This means that exposure error is much less serious for computed radiography at the time of image sensing and recording. However, image display apparatus have a much more limited dynamic range. Tone scale mapping in computed radiography can be specifically tailored to provide an optimal rendition of every individual image. However, most output media, such as photographic film and displays such as flat-panel or cathode ray tube (CRT) displays do not have wide enough dynamic range to display this information at nearly 10,000:1 latitude with proper visual contrast. It is, therefore, necessary to carefully allocate the available output dynamic range to display the clinically relevant part of the input code values.

Conventional methods for adjusting the intensity range and slope of radiography image values are generally not satisfactory for mammography. For general radiography, for example, methods that provide contrast improvement, such as those described in U.S. Pat. No. 5,633,511 entitled "Automatic Tone Scale Adjustment Using Image Activity Measures" to Lee et al., that constructs a tone-scale transfer curve, or disclosed in commonly assigned U.S. Pat. No. 6,778,691 entitled "Method of Automatically Determining Tone-Scale Parameters for a Digital Image" to Barski et al., generating a Look-Up Table (LUT) for obtaining a desired tone scale for an image using the slope of the tone scale curve over its mid-range densities, do not address the particular problems posed in mammography, but are better suited to more general x-ray images. Thus, for example, where mammography images for a patient taken at different times differ with respect to exposure values or other values, application of such contrast improvement techniques is not likely to provide consistent rendering that would allow more accurate assessment of condition changes by the evaluating clinician.

Contrast stretching is one method that has been proposed for providing a measure of normalization between images. For example, U.S. Pat. No. 5,357,549 entitled "Method Of Dynamic Range Compression Of An X-Ray Image And Apparatus Effectuating The Method" to Maack et al. describes a dynamic range compression technique that stretches image intensity in only a particular area of interest, such as within the lung area of a chest X-ray. In a similar approach, U.S. Pat. No. 5,835,618 entitled "Uniform And Non-Uniform Dynamic Range Remapping For Optimum Image Display" to Fang uses a method of dynamic range remapping for enhancing the image in both dark and bright intensity areas. Contrast adjusting methods such as these focus on improving the overall image appearance of individual images, which may in turn help to improve image consistency to some degree. However, these and other conventional contrast-stretching methods do not directly address inconsistency from image to image and do not address problems specifically encountered in mammography imaging.

Thus, although there have been some proposed methods for providing consistency in diagnostic image rendering, none of these methods addresses the particular problems posed by mammography. The problem of providing consistency in image appearance is complicated by a number of factors, such as by the number of different types of imaging systems that can be used, each having different preprocessing of the initial image data, by imaging techniques applied during the exam, and by viewer preferences for image content. It would be beneficial to provide solutions to the mammography rendering problem that provide consistent results for the same types of mammography images obtained at different systems, under different conditions, and at different times.

SUMMARY OF THE INVENTION

It is an object of the present invention to advance the art of diagnostic mammography imaging with respect to image consistency. With this object in mind, the present invention provides a method for rendering a mammography image, performed at least in part by a computer system. The method includes obtaining mammography image data for a patient and storing the image data in a computer-readable electronic memory; generating a mapping that transforms the image data to a predetermined output data space in which each input data code value corresponds to an output image data value by: estimating a relative amount of dense tissue from the mammography image data; identifying at least a first control point that delineates breast tissue from non-tissue image content and a second control point that delineates a fatty tissue region from a dense tissue region; allocating output image data values in the output data space for the identified fatty and dense tissue content according to the estimated relative amount of dense tissue; mapping image data values to the allocated output image data values according to the first and second control points; and rendering the mammography image on a display according to the generated mapping.

It is a feature of the present invention that it provides a method for improving the rendering consistency of mammography images based on establishing anchor points or control points related to tissue type, and allocating image data values suitably according to relative tissue density or amount. The information on the level of breast density in the image helps to guide the allocation of sufficient gray scale space for dense tissue, so that consistent contrast is maintained or controlled for a given amount of a given type tissue across images, and so that sufficient contrast can be given for better detection of lesions in dense tissue areas.

It is an advantage of the present invention that it adapts to different imaging apparatus and equipment with different image processing techniques, so that images taken at different times or on different imaging systems can be processed and compared against each other.

These and other objects, features, and advantages of the present invention will become apparent to those skilled in the art upon a reading of the following detailed description when taken in conjunction with the drawings wherein there is shown and described an illustrative embodiment of the invention.

BRIEF DESCRIPTION OF THE DRAWINGS

While the specification concludes with claims particularly pointing out and distinctly claiming the subject matter of the present invention, it is believed that the invention will be better understood from the following description when taken in conjunction with the accompanying drawings.

DETAILED DESCRIPTION OF THE INVENTION

The present description is directed in particular to elements forming part of, or cooperating more directly with, apparatus in accordance with the invention.

It is to be understood that elements not specifically shown or described may take various forms well known to those skilled in the art.

Reference is made to U.S. patent application Ser. No. 12/021,504 filed on Jan. 29, 2008, entitled "SENSITOMETRIC RESPONSE MAPPING FOR RADIOLOGICAL IMAGES", which published as US 2009/0190716, commonly assigned.

Reference is made to U.S. patent application Ser. No. 12/482,651, filed on Jun. 11, 2009, entitled "RENDERING FOR IMPROVED DIAGNOSTIC IMAGE CONSISTENCY" both by Huo et al., commonly assigned.

The term "DICOM destination" refers to a device on a DICOM (Digital Imaging and Communications in Medicine) network. By definition, a DICOM destination could be a display or an archival system, such as a PACS (Picture Archiving and Communications System) that uses one or more computers or networks dedicated to the storage, retrieval, distribution, and presentation of medical images. The most commonly used standard format for storage of diagnostic image data and related information is DICOM format.

In the context of the present disclosure, the term "dense tissue" is generally considered synonymous with fibroglandular tissue of the breast. Within the mammography image, this dense tissue is readily distinguishable from fatty tissue to those skilled in breast cancer diagnosis.

The present invention provides a tissue-based gray-scale normalization for consistent rendering of mammography images. The method of the present invention provides a remapping of density values for mammography images that provides consistent rendering of images that may have been taken at different times and under different conditions, including images obtained from different imaging systems and using different receiver types. Consistent rendering of images allows the clinician to more easily view and compare images for a more efficient and accurate diagnosis.

The processing of the present invention is performed, at least in part, on a computer or other type of control logic processor, such as a dedicated image processor, for example. In the context of the present disclosure, the term "networked processor" is used to identify the computer or other type of processor that executes programmed instructions for consistency control. The computer or other type of control logic processor that is used as the networked processor is equipped with and in communication with the needed electronic data storage and memory circuitry for executing programmed logic instructions and for storing results. The computer may include one or more computer-readable or computer-accessible electronic storage media, for example; magnetic storage media such as magnetic disk or magnetic tape; optical storage media such as optical disk, optical tape, or machine readable bar code; solid-state electronic data storage devices such as random access memory (RAM) or read-only memory (ROM); or any other physical device or media employed to store a computer program having instructions for controlling one or more computers and related data to practice the method according to the present invention. In general, the term "computer-accessible electronic storage medium" is used to mean memory or data storage media in general use for executing the processes of the present invention.

Figure 1A:
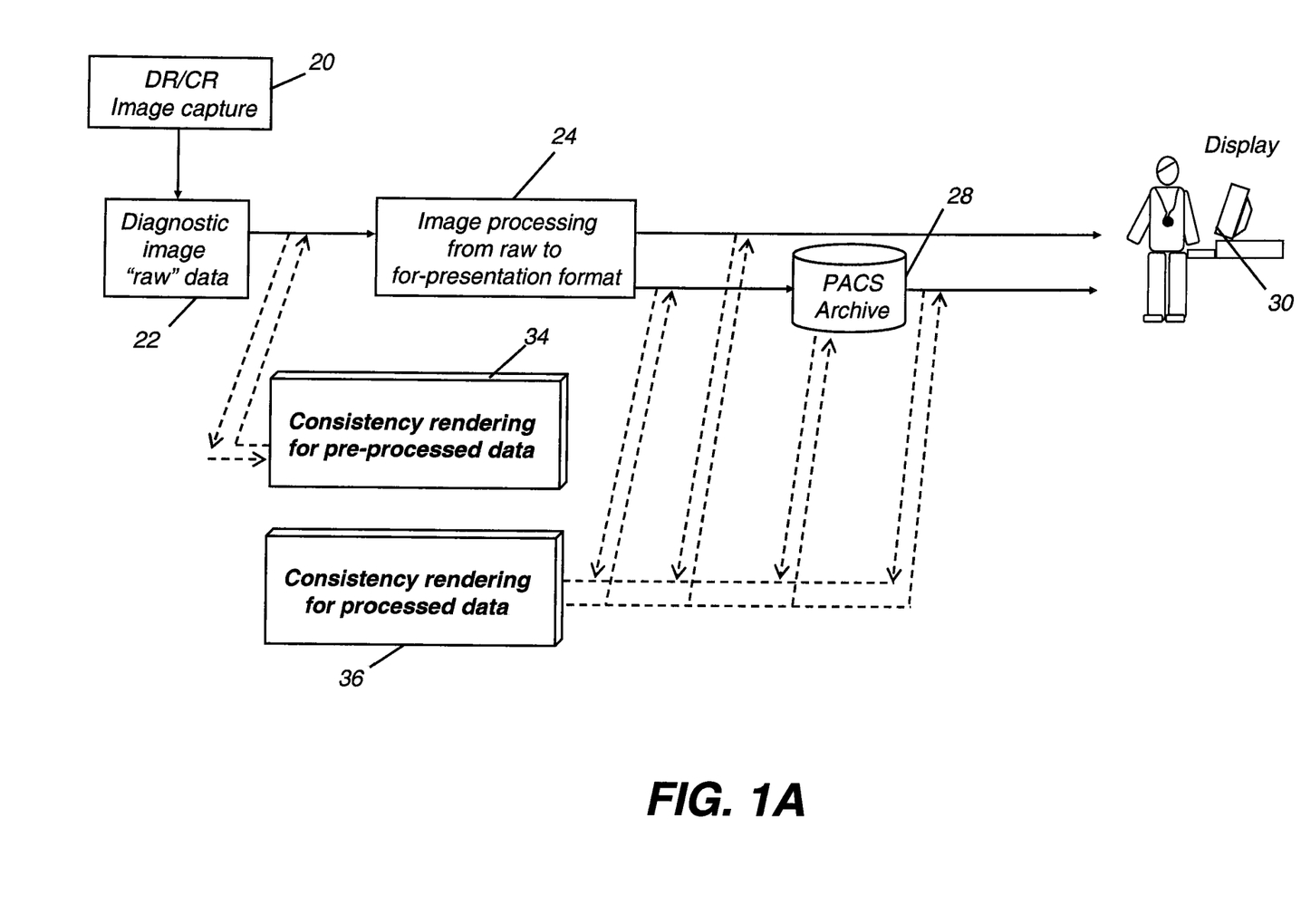
FIG. 1A is a schematic block diagram showing a systems solution for achieving improved consistent rendering of mammography images.

Embodiments of the present invention can operate on a single image, not requiring the use of multiple images for obtaining suitable image rendering parameters. In addition, the consistent rendering methods of embodiments of the present invention are not limited to one type of data or imaging system but can be applied either to pre-processed or "raw" image data directly as obtained from a DR or CR system or film scanner, or to processed data that has been readied for display or printing. Referring to FIG. 1A, there is shown a block diagram of the imaging chain for captured mammography images, with the possible points of access to consistent rendering software provided in embodiments of the present invention. The programmed software modules for data processing to provide consistency control shown and described with reference to FIG. 1A execute on one or more networked computers or other logic processors, according to programmed instructions.

Figure 1B:
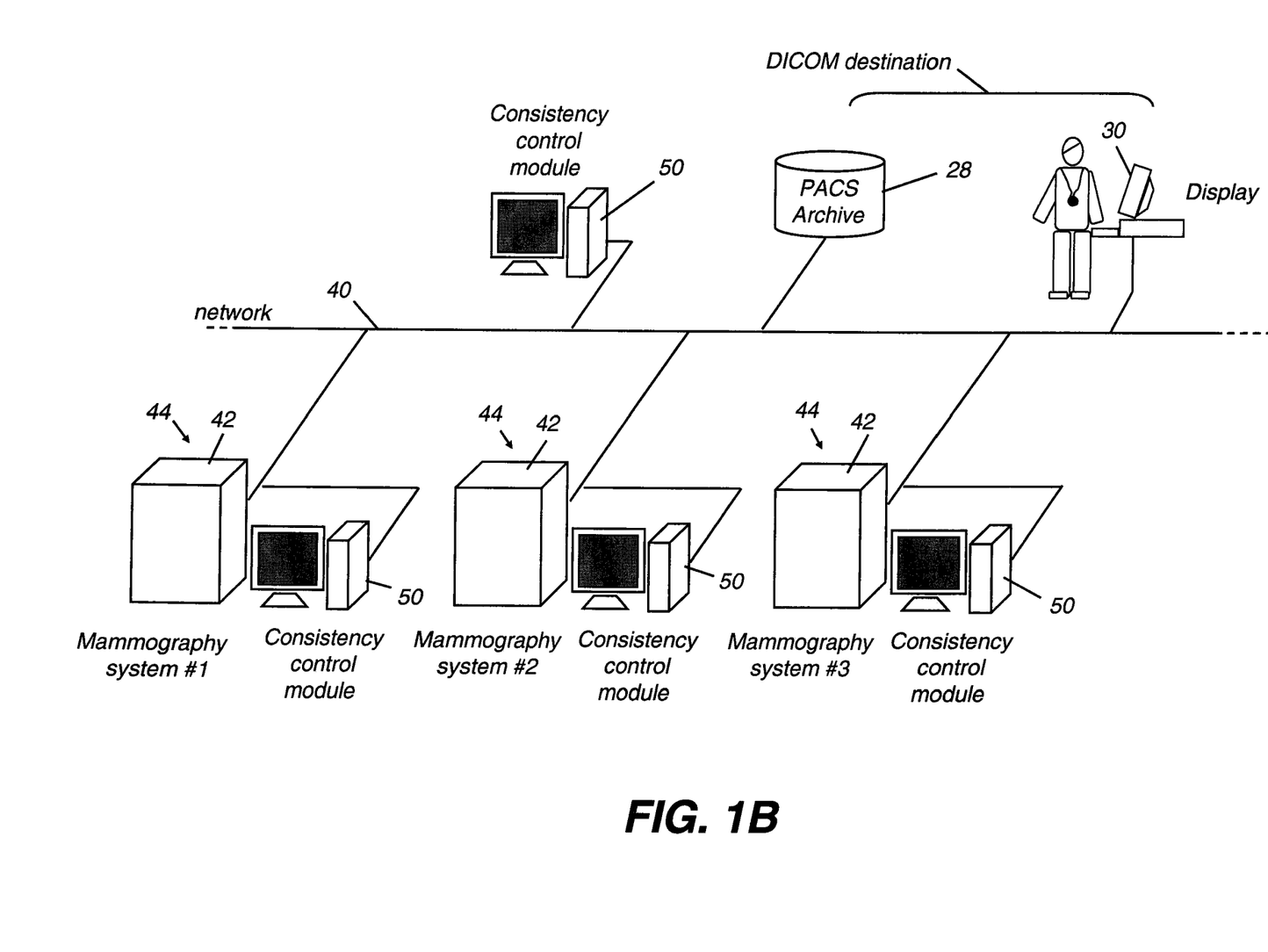
FIG. 1B is a block diagram showing a network with a number of consistency control modules at different networked locations in one embodiment of the present invention.

Tracing the basic image processing chain in FIG. 1A, an image capture device 20 obtains and stores, in a computer-readable electronic memory, unprocessed or "raw" mammography image data 22 that is processed by an image processing system 24 and is provided directly to a networked DICOM destination, which could be either a display 30, as shown in FIGS. 1A and 1B, or a PACS archival system 28, for example. A consistent rendering processor 34 can optionally be provided for providing consistent rendering to the pre-processed data. Alternately, an optional consistent rendering processor 36 can be provided for handling processed data and archived data that may have already been rendered. As represented in FIG. 1A, this processing can include image data accessed at any of a number of points along the imaging chain, including prior to or following PACS archival. The consistency rendering of the present invention can be used in any of a number of embodiments, including with any of a number of types of different image capture devices 20.

In the block diagram of FIG. 1B, a network 40 connects with a number of mammography imaging sites 44 and with PACS archival system 28. Each mammography imaging site 44 shown in the embodiment of FIG. 1B has a corresponding consistency control module 50 for images obtained at a mammography imaging system 42. Consistency control module 50 may also be independent of any specific imaging system 42 and located at any accessible networked location, so that it is effectively in communication with more than one imaging system 42. Consistency control module 50 can execute within a specific host computer or other control logic processor or may be a network program that executes on a remotely located, networked server. As a hardware or software component, consistency control module 50 receives and executes entered and stored programmed instructions to identify information such as imaging source, detectors, and their manufacturers, and to identify tissue types from within the image, to obtain and determine the necessary control parameter values for the image, to process the image using the control parameters for remapping image data, and to provide the processed, rendered mammography image as output.

Network 40 can be any suitable network type, including an Ethernet network, for example. This may be a proprietary local area network (LAN) located within a hospital or other facility or may be an internet-accessible network with appropriate security safeguards for privacy of patient data.

With the modular control logic arrangement shown in FIG. 1B, consistency can be obtained according to a standard that is stored on the network and used by each consistency control module 50. Alternately, a number of consistency variables or parameters can be stored and used, including consistency parameters specific to each mammography imaging system 42. This enables consistency between systems, so that the image obtained and displayed from imaging system #1 can have consistent appearance with an image obtained and displayed from imaging system #3, for example. Significantly, two images taken at different times can be provided with consistent rendering in order to facilitate their comparison.

Figure 1C:
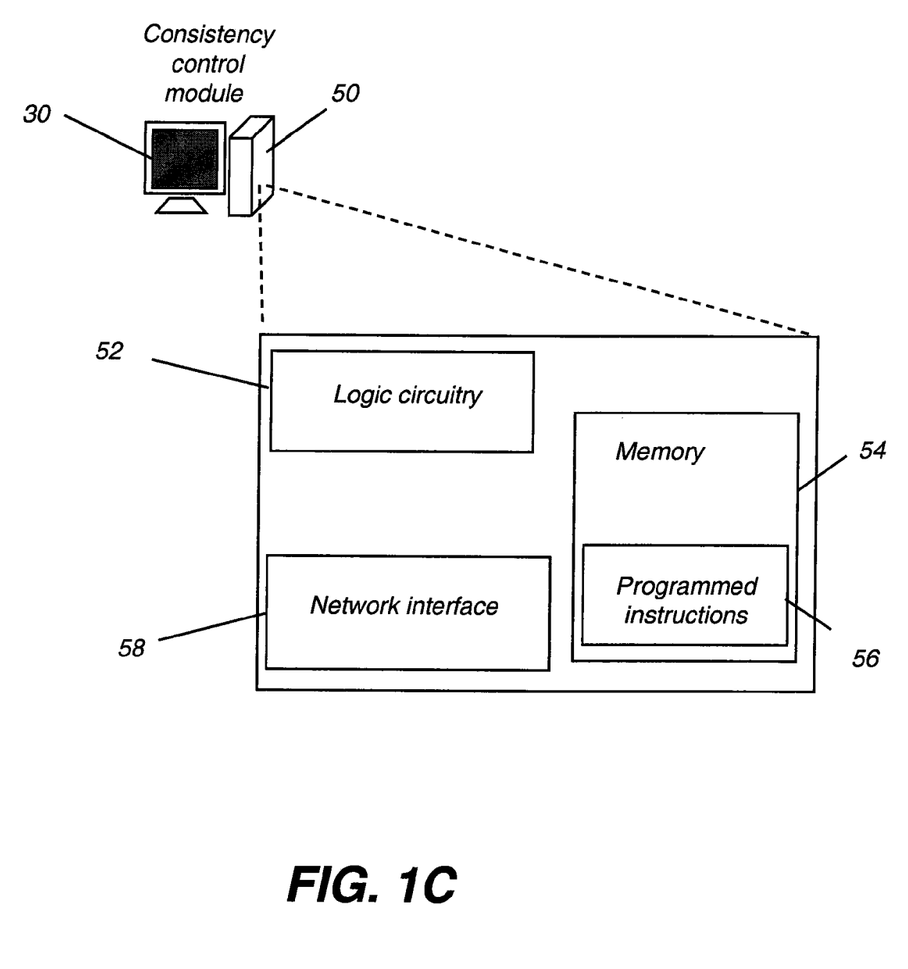
FIG. 1C is a schematic block diagram that shows components that execute functions of consistency control on a computer or other processor.

The schematic block diagram of FIG. 1C shows control logic components that execute functions of consistency control module 50 on a computer or other networked processor. Logic circuitry 52 provides the control logic that operatively responds to and executes instructions 56 that are stored in a memory 54. A network interface 58 then enables communication of un-processed and processed image data over the network. The stored instructions are a set of programmed instructions that can include instructions for obtaining an image from a networked apparatus; instructions for determining and obtaining variable control parameters and values; instructions for identifying one or more control points in the obtained digital image data; instructions for mapping the input code values of the one or more control points to corresponding predetermined code values; instructions for mapping additional input code values to output values according to the one or more control points; instructions for rendering the mammography images; and instructions for providing rendered image data as output. Rendered mammography images are then directed to a DICOM destination, such as display 30 that may be located at any suitable point in the network for viewing by the diagnostician. An alternate DICOM destination would be a PACS or other type of archival system.

Figure 2:
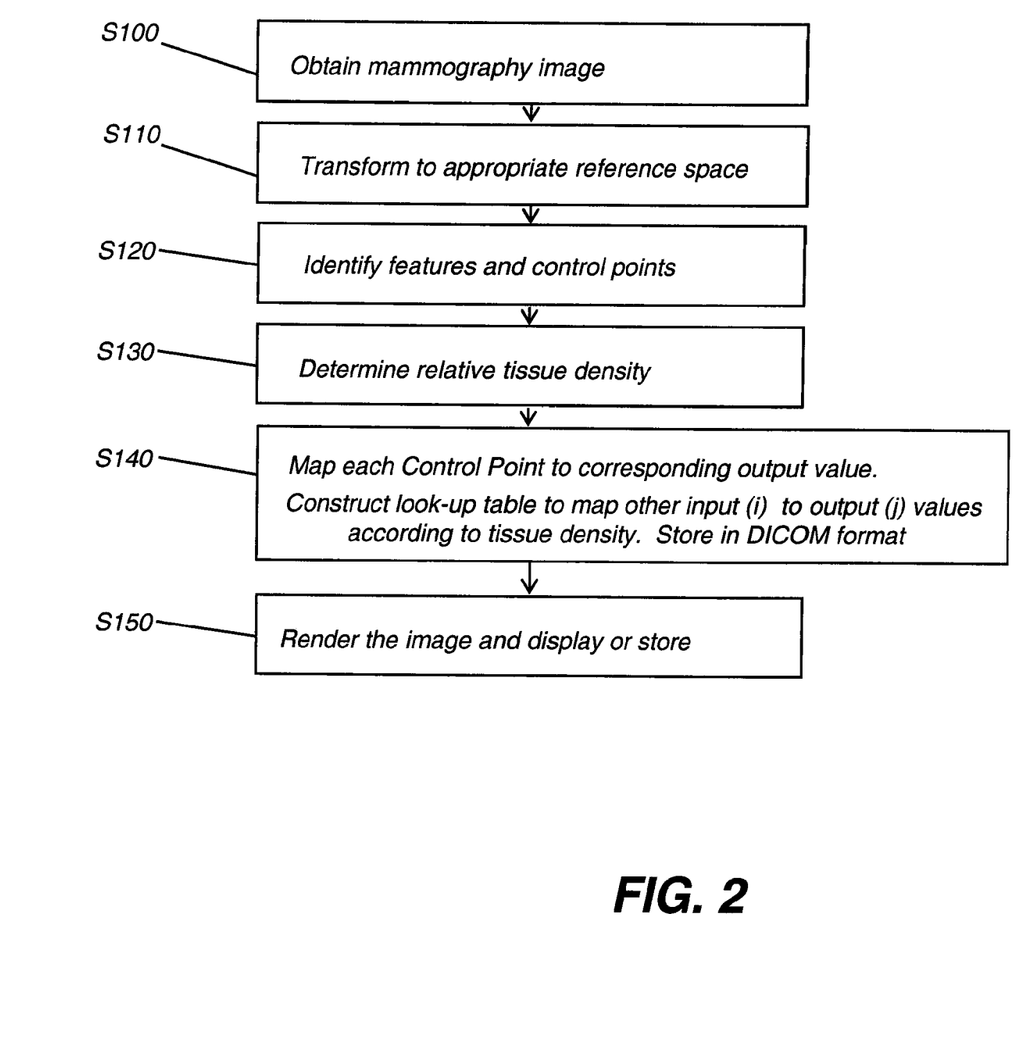
FIG. 2 is a logic flow diagram showing consistent rendering processing according to one embodiment of the present invention.

The logic flow diagram of FIG. 2 shows processing that is executed for consistent rendering by consistency control module 50 in one embodiment. In an initial step S100, the image data for a mammography image is input to consistency control module 50 (FIG. 1C). This step also obtains any needed information on the originating imaging system type (DR/CR/film), manufacturer, and other image metadata. A transform step S110 follows, in which the image data is transformed to the appropriate reference image data space, as necessary. This may include, for example, transforming the data to a log-density reference space, similar to that used for photosensitive film media, or to a linear reference space that is generally more often used for digital image detectors. Transform step S110 may or may not be needed, depending on the metadata obtained in step S100. A control point identification step S120 is then executed, in which the anchor or control points for consistent rendering are identified within the image data. A density determination step S130 determines the relative tissue density, information needed in order to map image data relative to the identified control points. A mapping step S140 then performs the needed mapping of control points to output points in presentation space. This data is then used to form a Look-Up Table (LUT) that stores the needed data values for 1:1 value mapping and rendering. The LUT is then used in a rendering step S150 for rendering the mammography image in a consistent manner. More detailed description, given subsequently, expands on the functions and operations executed within each step.

Transform Step S110

Figure 3:
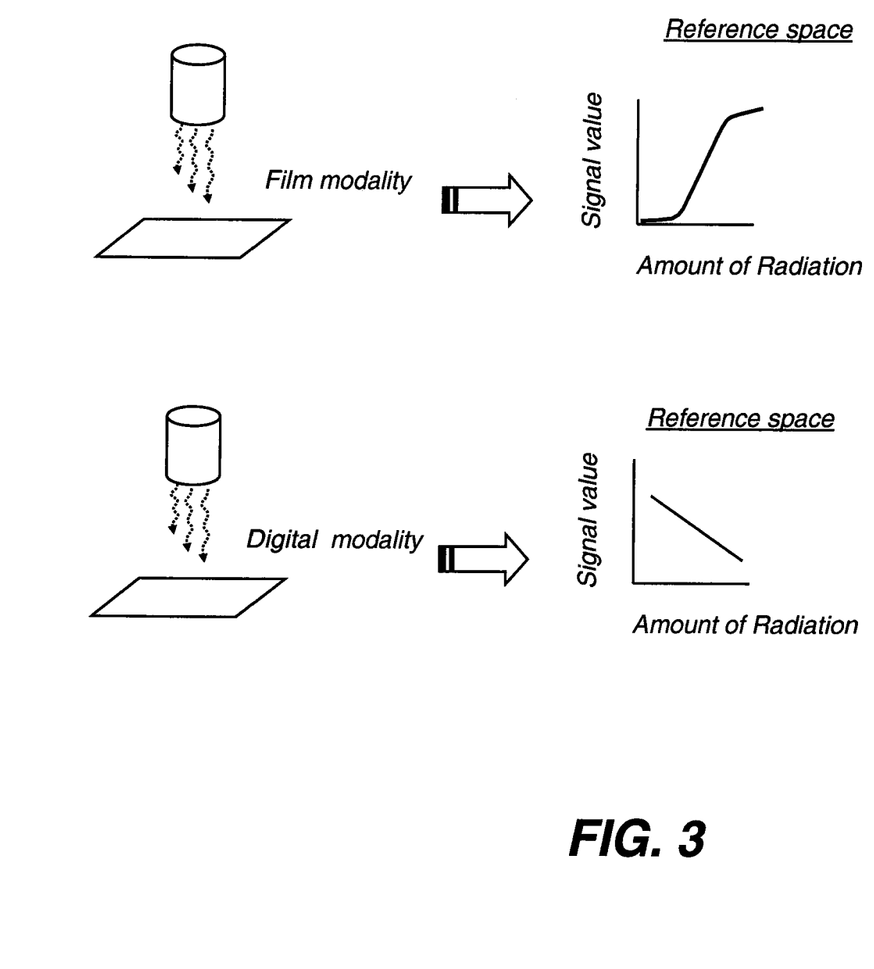
FIG. 3 is a schematic diagram showing some typical sensitometric response characteristics of different imaging modalities.

In order to provide consistency in image rendering, it is necessary for the image data to be in the proper image space, that is, sensitometric response space. The sensitometric response relates the amount of radiation received (conventionally plotted along the abscissa or x-axis of the graph) with the signal value that is obtained (conventionally plotted along the ordinate or y-axis of the graph). As shown at the top of FIG. 3, film shows a sigmoid response curve, wherein the signal value relates to optical density (OD). Digital receivers typically exhibit some other characteristic response, including a more linear response as suggested at the bottom of FIG. 3, and provide an altogether different type of signal value. Because there can be a number of different types of film scanning or digital imaging systems, including both CR and DR mammography imaging systems, each having their own sensitometric characteristics, some type of initial image normalization is available in order to proceed with the balance of the processing needed for image consistency. Methods for providing this image data transformation to a common space from any of a number of different types of imaging systems are well known to those skilled in the imaging arts.

Control Point Identification Step S120

Figure 4A:
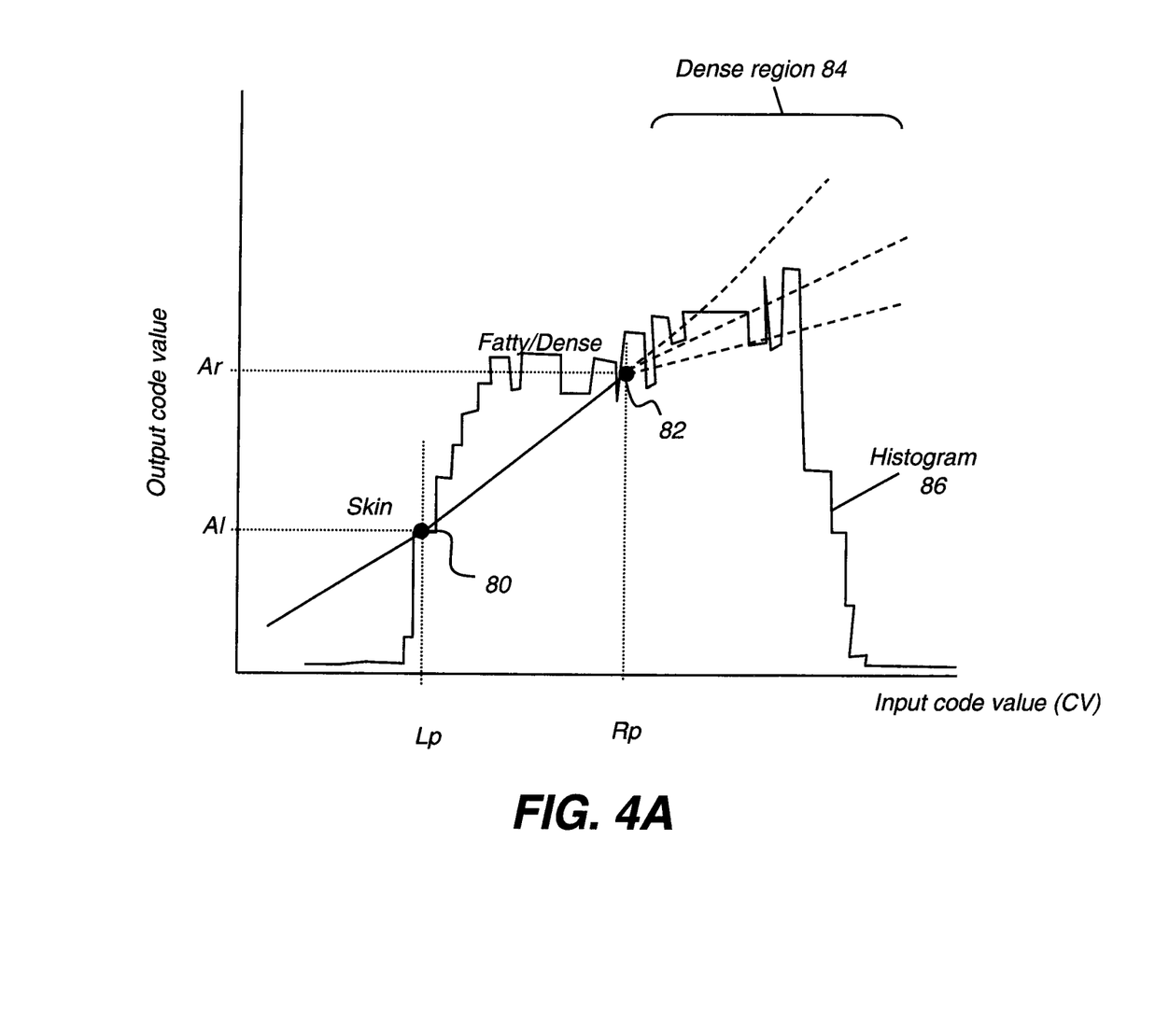
FIG. 4A is a graph showing mapping of input to output code values using two control points in one embodiment.
Figure 4B:
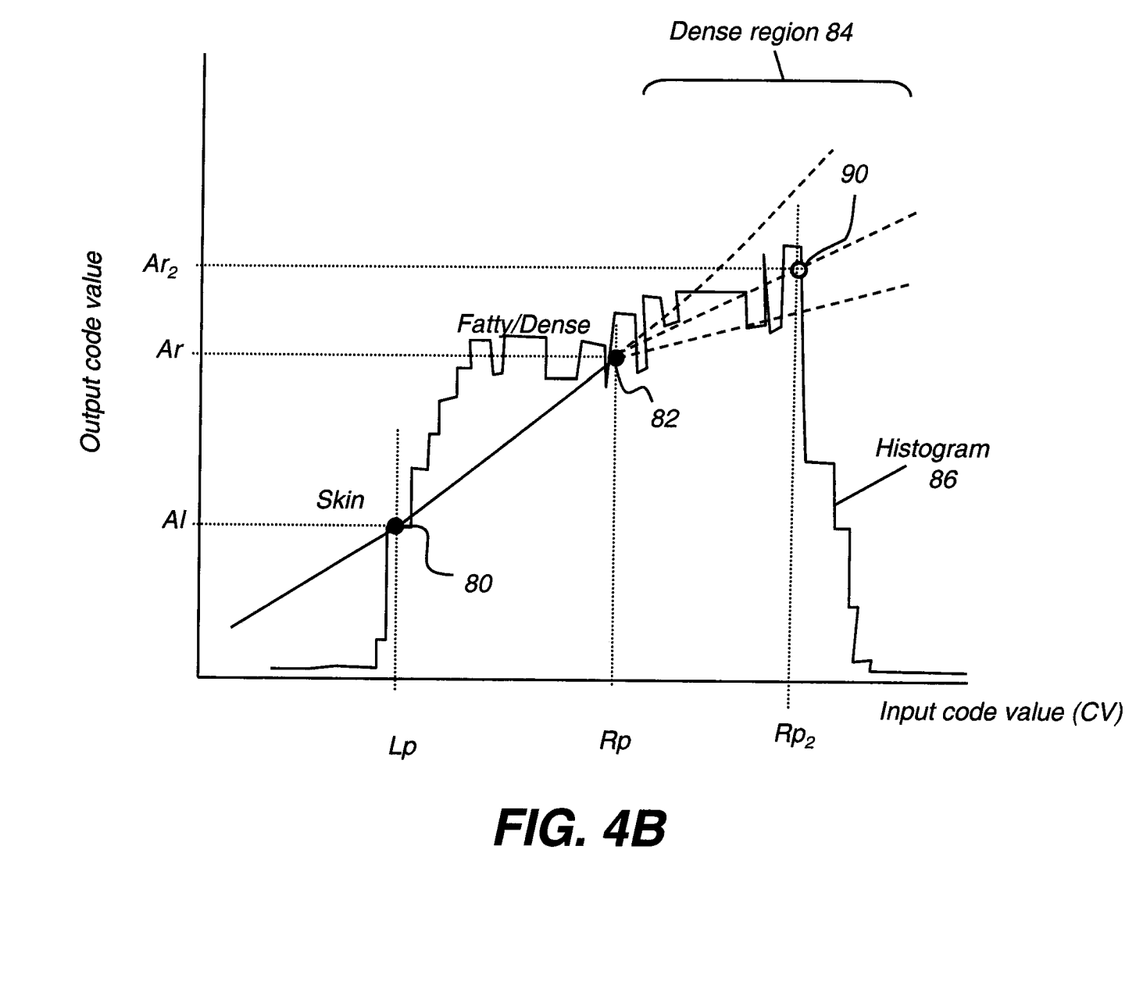
FIG. 4B is a graph showing mapping of input to output code values using three control points in an alternate embodiment.

The method of the present invention analyzes the mammography image data in order to segment breast tissue from background image content and to identify a set of control points for mapping to the output code value in the image presentation space. Each control point relates to a threshold for breast tissue. Referring to FIG. 4A, there are shown the two control points 80 and 82 that are needed in embodiments of the present invention. FIG. 4B shows an alternate embodiment that uses three control points 80, 82, and 90. Additional control point 90 may be a threshold, such as a threshold denoting the top 1 or 2 percent of histogram values to remove some artifacts, but may alternately be a point within a dense region 84 that is used to help determine the mapping over the dense region. Depending on the mapping mechanisms used at the tail (i.e., input value<lp) and shoulder (i.e., input value>Rp2), additional control points such as max and min values of the input image may be required to maintain the consistency of the overall brightness.

Figure 5A:
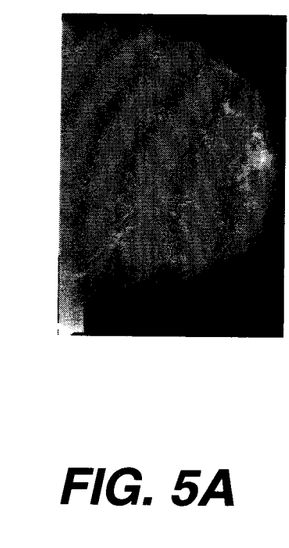
FIG. 5A is a mammography image after initial processing.
Figure 5B:
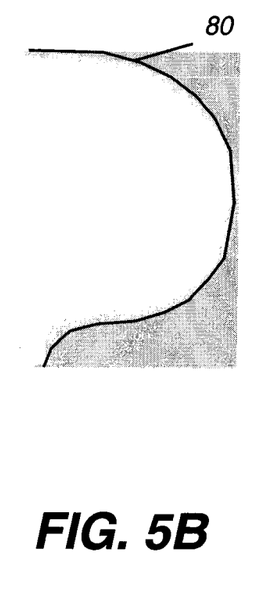
FIG. 5B is a mammography image with the skin line feature highlighted.
Figure 5C:
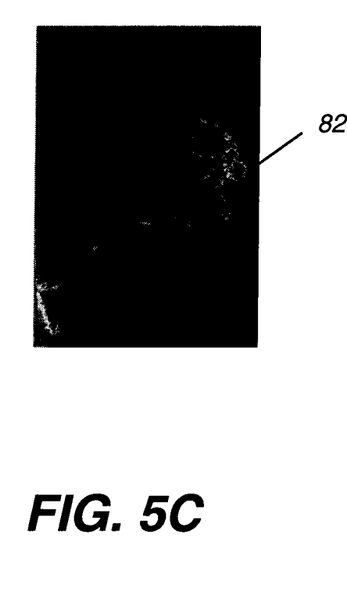
FIG. 5C is a mammography image showing dense tissue.

For reference in the following description, plan views of exemplary images are shown in FIGS. 5A, 5B, and 5C. FIG. 5A is a processed image. FIG. 5B shows skin line portions. FIG. 5C shows dense tissue, differentiated from the balance of fatty breast tissue.

A histogram 86 is shown in graphs of FIGS. 4A and 4B. The first control point that is identified is a skin line or skin line area threshold control point 80. This control point corresponds to a code value (CV) that defines a skin line or skin line-area along the periphery of the breast. In the nomenclature used in FIGS. 4A and 4B, skin line or skin line-area threshold control point 80 has the code value Lp (left point). In the output code space, value Lp maps to value A1. Points outside the skin line could remained unprocessed. Points with a value lower than the skin-line area threshold can be treated differently.

The second control point is a dense threshold control point 82 that is used to distinguish fatty tissue from dense tissue. Dense region 84 includes code values higher than dense threshold control point 82. Mapping of values within dense region 84 to output presentation space depends on a number of variables, as described subsequently. The input code value corresponding to control point 82, designated Rp (right point), maps to value Ar in the output value space.

A third control point, shown in FIG. 4B, is a dense region control point 90. This added point can be used to help determine a slope or other relationship of values within dense region 84. The input code value of control point 90 is designated $Rp_2$ and maps to output code value $Ar_2$. Control point 90 is within dense region 84, but may or may not bound the region as a threshold value. The output range for the input range between Rp and $Rp_2$ can be proportionally related to the amount of percent dense tissue identified in the breast region. Percent density can be expressed as a ratio of dense tissue to total tissue content.

In one embodiment, the control point or points are simply determined using a histogram of image values, for example. Variable control parameters that determine the desired output values for mapping digital image data can be obtained in a number of ways, including the use of template images, the use of learned values from testing of diagnostician preferences over time, and the employment of arbitrarily assigned values, such as values preferred by a particular diagnostician, for example. Mapping to the image presentation space is monotonic and may use predetermined code values, that is, pre-selected or pre-calculated code values, to define output boundaries.

Control points (CPs) for consistency mapping can be selected for their relative significance based on factors such as: (i) empirical experience, (ii) clinical relevance, or (iii) viewer preference. Empirical experience, for example, may indicate that a specific value works best for presenting specific types of tissue. Clinical relevance bases CP determination on factors such as the relative relevance of particular tissue to diagnostic requirements. Viewer preference can be based on factors such as contrast settings or overall brightness or darkness by selecting proper control points and their values. Control points and their values can be predetermined or determined based on the analysis of each image. In one embodiment, control points 80, 82 and 90 are generated from a histogram analysis and can vary from one image to the next; control points can also be generated from image segmentation of the breast from background and of dense tissue from fatty tissue.

By identifying control points 80, 82, and (optionally) 90, step S120 (FIG. 2) provides the relationship needed to map input code values for a portion of the mammography image data to output code values for consistent rendering. Input code values can be from a mammography image taken on any type of system and from any type of receiver, including DR, CR, or scanned film. Once the data values that define control points 80, 82, and 90 can be identified, the fatty portions of the breast can be re-mapped for consistent rendering in a subsequent step. Similarly, once control points 82 and (optionally) 90 can be identified, dense portions of the breast tissue can be re-mapped appropriately. Each region of the image data can have a mapping that is independent of the mapping for other regions.

Control points can be based on predetermined fixed values, as noted earlier. In one embodiment, default values are initially defined, then adjusted slightly to allow a measure of variability according to any of a number of factors. Thus, for example, a given percentage density value may be selected as a default control point. However, control points may be separately computed for each image, based on its distribution of image data values, for example.

Background segmentation, executed as part of step S120 as shown in FIG. 2, enables the image tissue content to be identified and separated from background content, so that both types of image content can be handled separately. There are a number of approaches to background segmentation, well known to those skilled in the imaging arts. The overall goal of background segmentation is to define the tissue portion of the image, isolated from non-tissue background areas. Among well known approaches are histogram analysis and manipulation, for example.

Figure 6:
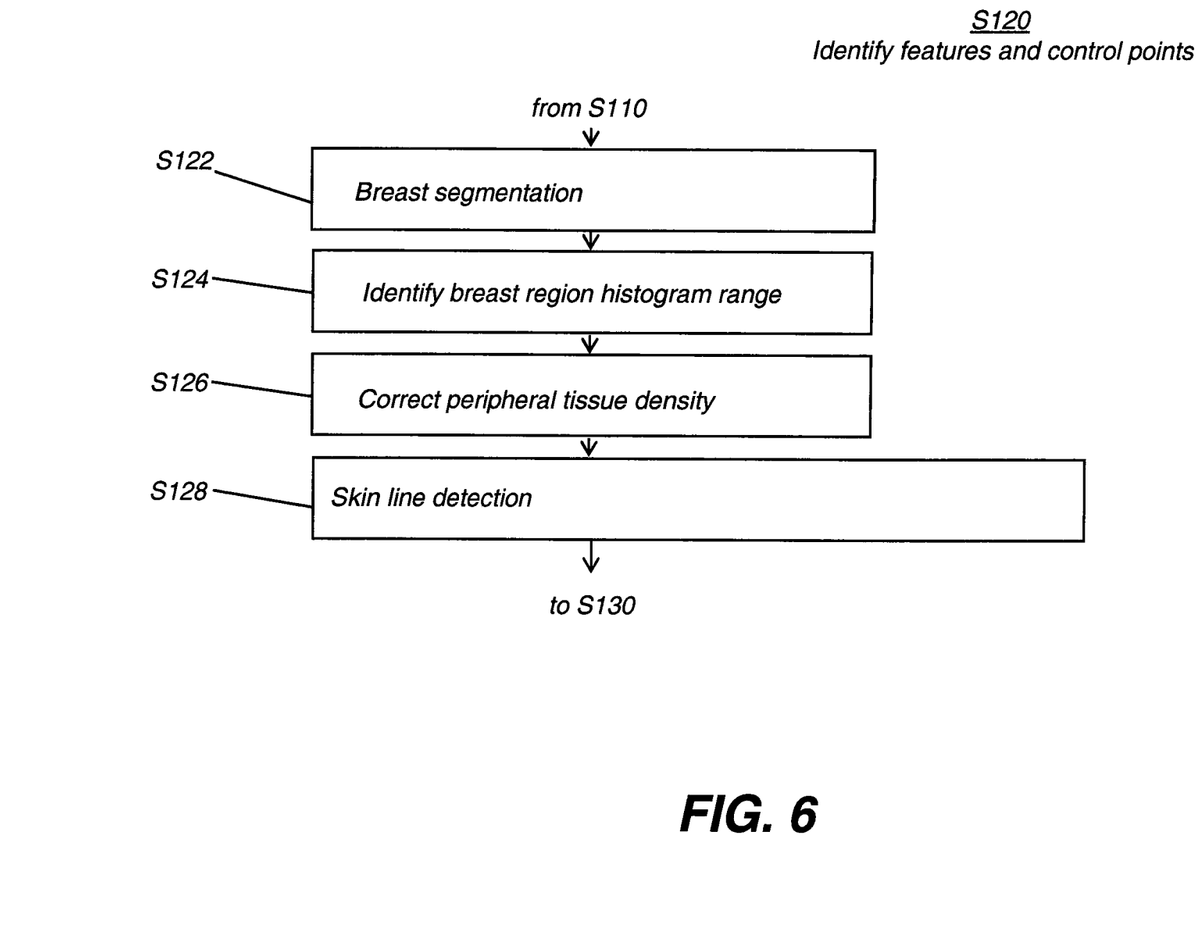
FIG. 6 is a graph showing substeps for a process of identifying features and control points in one embodiment.

The logic flow diagram of FIG. 6 shows portions of control point identification step S120 in one embodiment. A breast segmentation step S122 performs segmentation of breast tissue from background content, using well-known segmentation techniques to identify pixels within the breast region. A histogram range identification step S124 then correlates the segmentation information with the range of breast image data values. An optional peripheral correction step S126 performs density correction for skin line breast tissue. This correction is particularly useful where a display monitor is used with mammograms from digital radiography DR systems, since the display screen has a reduced dynamic range when compared to film, for example. Peripheral correction is described, for example, in an article entitled "Density Correction of Peripheral Breast Tissue on Digital Mammograms" by Ulrich Bick, et al. in *RadioGraphics*, November 1996, pp 1403-1411. A skin line detection step S128, using peripheral correction data, then more clearly identifies skin line content for improved visualization and processing.

Density Determination Step S130

While the re-mapping of fatty tissue code values to a consistent output rendering space can be seen as somewhat straightforward, as shown in FIGS. 4A and 4B, the problem of re-mapping dense tissue is more complex and has more variables. The function of density determination step S130 is to provide a measure of overall breast tissue density and density distribution that can be used to influence the mapping process that follows.

Methods for density determination and classification are described in more detail in commonly assigned U.S. patent application Ser. No. 12/471,675, filed May 26, 2009, entitled "ASSESSMENT OF BREAST DENSITY AND RELATED CANCER RISK" by Huo et al. Techniques available for this purpose include homogeneity mapping and density probability mapping, both described in the referenced application. Density probability map generation combines the sums of Gaussian-weighted intensities of tissue pixels within a region. This type of map indicates the relative likelihood that any particular pixel will be within the dense region. The density probability map can be generated by determining mean, standard deviation, and other statistical values from a known region of highly dense tissue, then calculating weighted density probability for each pixel outside the highly dense region. Various other types of statistical density determination could alternately be used to provide a measure of breast density. The relative percent of dense tissue to other breast tissue is another useful density metric.

Mapping Step S140

Figure 7:
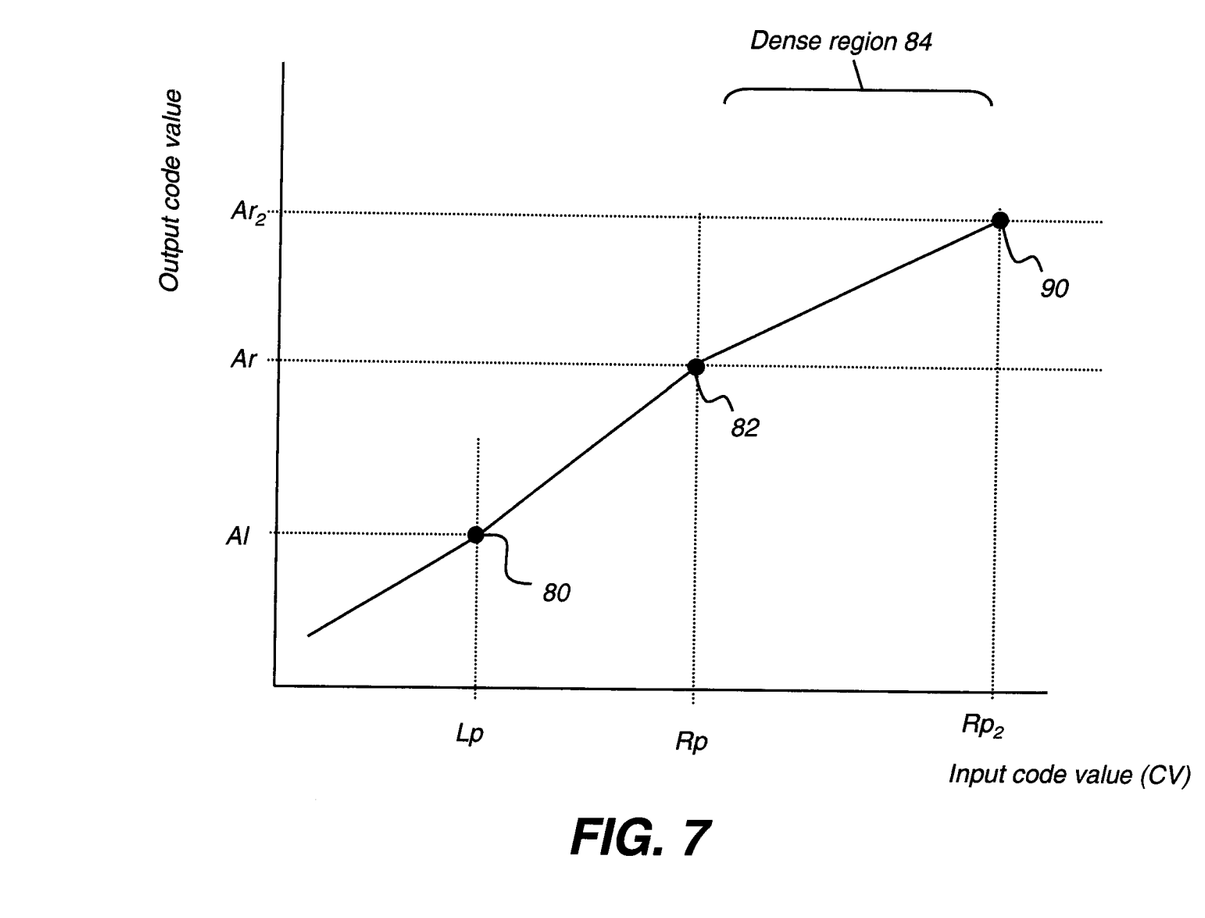
FIG. 7 is a graph showing mapping of input to output code values and including mapping of the dense region.

Given the control points identified in step S120 and the breast density quantification obtained in step S130, the 1:1 mapping of input code values (i) to output code values (j) for improved consistency can be performed. Mapping step S140 (FIG. 2) performs this re-mapping of code values, as shown in FIGS. 4A and 4B. Skin line or skin line area threshold control point 80, dense threshold control point 82, and dense region control point 90 provide three possible control points as anchor points for the remapping, helping to standardize the image rendering regardless of the original mammography system and receiver media. FIG. 7 shows a linear relationship used for data values between points 80 and 82 in one embodiment. In practice, a mapping other than linear could be used. When input and output ranges are set, the relationship between input and output values is determined if a linear relationship is applied.

Remapping of dense region 84 (FIGS. 4A and 4B) is of particular value for mammography. Calcifications and very dense masses are particularly visible in the high-end pixel intensity values. Allocation of these values can be in a linear or non-linear, but monotonic arrangement, depending on the extent of the dense region, a factor of the amount of density variation, and depending on the distribution of the image data values for dense tissue. In one embodiment, the output range for fatty area tissue is fixed for all images, while the output range for dense area varies depending on the percent dense tissue identified for each image. In another embodiment, the allocated output ranges for both fatty (Lp, Rp) and dense (Rp, Rp2) tissue are proportional to the percent fatty and percent dense tissues are identified for each image.

As part of mapping step S140 in FIG. 2, Look-Up Tables (LUTs) can be generated and stored for rendering each of the one or more images submitted in initial step S100, providing consistent rendering by a remapping of the initially processed mammography image data values. As part of the mapping, an adjustment can be made for each mapping, depending on image capture variables or other parameters, such as adjustment for variation in breast positioning, for variation in image exposure, and for variation with different types of pre-processing by different imaging system manufacturers, for example. Image-specific adjustments can be made to the remapping values based on analysis of the obtained mammography image data and can depend on image content or on maximum and minimum or other relative pixel data values, on dynamic range, on mean or median or other computed statistical value, on aspects of the imaging technique or imaging equipment used to obtain the image, on patient condition, on demographics, on medical history, or on patient positioning. For example, an adjustment can be computed based on the average brightness of pixels within a portion of the ROI. Alternately, image-specific adjustments can be empirical, based on the experience of the viewing practitioners or of those who administer the imaging system. In still other embodiments, image-specific adjustments can be made by comparing the obtained image data with an electronically stored template image that has been selected beforehand. For example, this may include contrast adjustment that adjusts image content for very dark and very light regions.

The diagram of FIG. 7 shows the monotonic mapping of two points in the data, left point Lp and right point Rp to corresponding remapped output code values Al and Ar, respectively. For this example, left point Lp corresponds to the skin line threshold; right point Rp corresponds to the fatty/dense threshold. The slope of the remapped values is the quotient of relative distances (Ar-Al) divided by (Rp-Lp). In general, this slope value can change over the range of image values. In one embodiment, output code values Al and Ar are fixed, limiting the range of slope values that are used. A slope value can be assigned or a slope constraint can similarly be imposed. The range between Al and Ar can depend on the percent of fatty tissue in the image, which is the ratio of fatty area over the whole breast area.

The mapping of values in dense region 84 can follow the slope established in the fatty tissue region between control points 80 and 82 or between either of these control points and control point 90. Alternatively, the mapping could be a function of some other value, such as relative activity level within the image, for example, which can have some diagnostic significance, particularly when considered with relation to spatial correlation. As is well known in image processing, an activity level, rate (i) can be calculated for each input pixel i. This can be used to determine value range allocation for mapping.

Factors that affect allocation of dense region 84 can include the following:

(i) Assigned range Al-Ar and balance of output code value space available, up to some maximum value $Ar_2$ or, alternately, Wr.

(ii) Slope limitations for mapping, generally empirically determined.

(iii) Activity rate and spatial correlation for a range of pixels.

(iv) Calculation of relative density, such as percent density, for the breast tissue. For patients who exhibit highly dense breast tissue, allocation of additional output data space in dense region 84 is generally advantageous.

Spatial correlation can be used to adjust LUT values appropriately for enhancing contrast for features of interest. A method such as spatial correlation histogram equalization (SCHE), described in commonly assigned US Patent Application Publication No. 2007/0269106 entitled "Method for Enhanced Visualization of Medical Images" can be applied for local and global contrast enhancement.

It is noted that methods and algorithms for identifying regions of interest in a diagnostic image are known to those skilled in the diagnostic imaging arts, as well as various techniques for mapping digital data in an input range within a region of interest to an output range. To existing methods, the method of the present invention adds adapting the dense and/or fatty regions of the pixel mapping differently from one image to the next, based on the relative distribution of dense tissue data that exceeds dense threshold control point 82.

Figure 8:
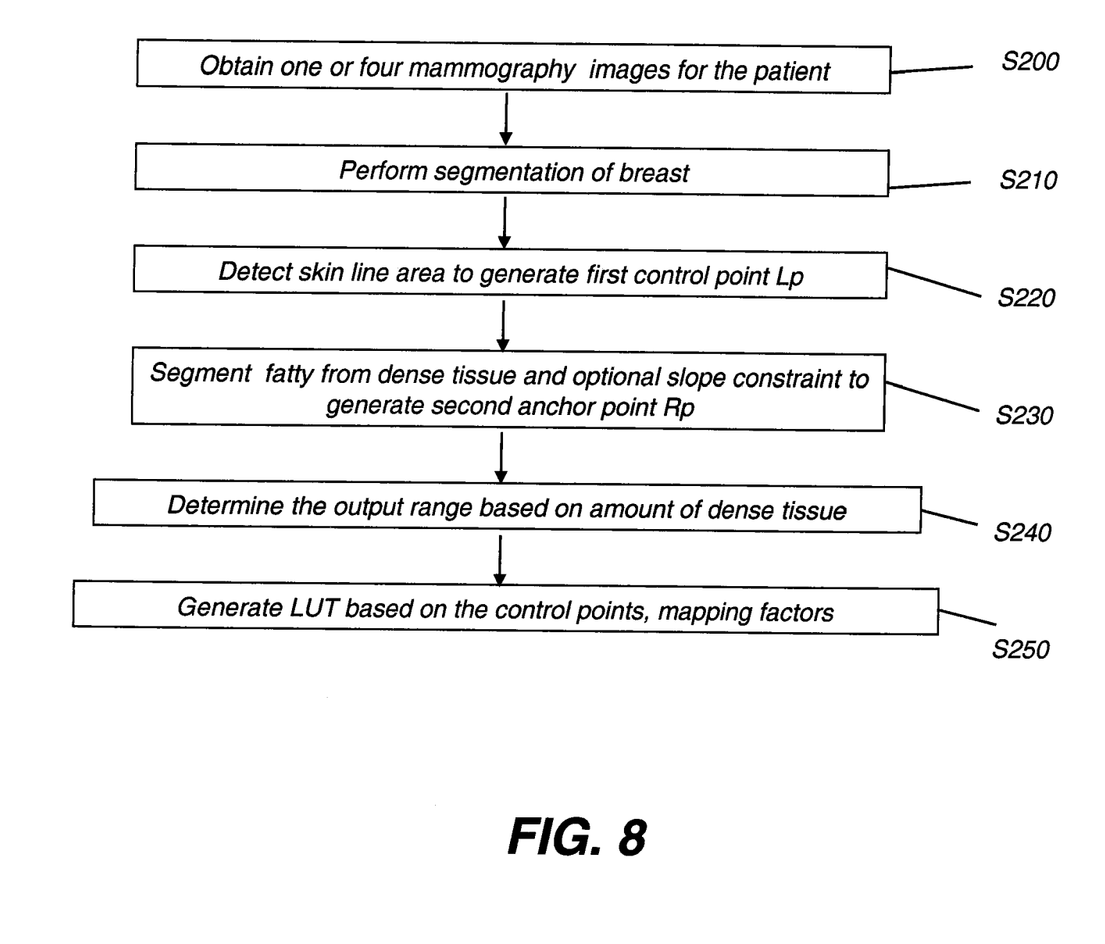
FIG. 8 is a logic flow diagram showing a sequence of steps for look-up table (LUT) generation according to one embodiment of the present invention.

The logic flow diagram of FIG. 8 shows a sequence of steps for LUT generation using anchor points in one embodiment. In an acquisition step S200, a mammography image, or a set of mammography images for the same patient, are provided to the executing program logic. Where a set of four images is obtained, the steps that follow can be executed on each individual image or on some portion of the other images. A segmentation step S210 provides segmentation of the breast from background and surrounding features. A skin line detection step S220 then determines the location of the skin line and provides a first anchor or control point, as shown earlier in FIGS. 4A-5B. A second segmentation step S230 segments fatty from dense tissue to define a second control point. The optional third control point, as shown in FIG. 4B, can be determined based on the amount of dense tissue, for example. At step S240, the output range is determined based on the amount of dense tissue. A LUT generation step S250 forms the LUT according to the identified anchor or control points, activity rate, and other variables.

In an alternate embodiment, the slope between corresponding control points within each region is used in order to provide the needed relationship for mapping of values. With reference to FIG. 7, for example, a linear relationship of input code values to output code values applies for each region. The control points that bound the region determine the slope s of the input:output mapping. Adjustment of output control points may be required based on constraints set on the slopes. Here, for mapping an input code value i to an output code value j, over the dense region:

$$j = Ar + s(i - Rp)$$

Alternatively, an activity rate determination calculates an activity rate over the dense region to determine the relationship between i and j.

Once the LUT or other type of mapping is generated, it can be stored in electronic memory or other computer-accessible electronic storage media, associated in some way with its corresponding mammography image or images. In one embodiment, the LUT is stored on the DICOM server itself or in some database related to DICOM or PACS image content, and is associated with the corresponding mammography image data for example. In one embodiment, this association is also encoded and stored as an entry in a database that is part of a DICOM installation. In another embodiment, this association is provided in the filename of the file containing the LUT and related image processing data. In yet another embodiment, one or more LUTs are stored within the DICOM header of the image data file.

Using the method of the present invention, a diagnostic image can be provided with more than one LUT, so that it can be compared against other images that were similarly prepared. In this way, each LUT provides an alternative image presentation. Thus, for example, different LUTs might be used to provide a consistent look suitable for different display apparatus or corresponding to different sets of viewer preferences. LUT data is stored along with peripheral tissue enhancement data in one embodiment, enabling enhanced visibility of breast tissue when displayed on a display monitor, for example.

Image Rendering Step S150

In image rendering step S150 (FIG. 2), the image data that has been processed for improved consistency is then displayed on a display monitor. The processed image data is also stored for future recall and display in a PACS or other storage system.

Using the method of the present invention, one or more mammography images taken from the same patient, at any of a number of different systems and with different equipment settings, can be provided with consistent treatment, so that evaluation of a single image or comparison of two or more images, either visually or using CAD assessment utilities, can be facilitated. The images can be sent to the consistency control module from the capture device or from any other DICOM destination. The methods and apparatus of the present invention can help to provide improved diagnosis of breast cancer. Particularly well suited to support longitudinal tracking, the methods of the present invention can be used to provide imaging and other data in a chronologically sequenced arrangement, helping the clinician to be alerted to changes in the condition of a patient that can be detected using image and measured data. The present invention helps to standardize the presentation of mammography image data so that information can be provided to medical personnel in a form that is straightforward to understand and to use. As was noted earlier, the method of the present invention provides pre-processing for one or more images, enabling a more accurate comparison between images that may have been taken at different times, by different operators, or under different imaging conditions. In one embodiment of the present invention, an image processing system performs the consistent rendering processes described earlier, then provides further enhancement for one or both of the consistently rendered images.

In embodiments of the present invention, consistent rendering is a networked function, able to handle the diagnostic image data at any of several points in the imaging process. Consistent rendering modules can be programmed to handle raw data or rendered data, including image data stored in an image archival system.

The invention has been described in detail with particular reference to certain preferred embodiments thereof, but it will be understood that variations and modifications can be effected within the scope of the invention as described above, and as noted in the appended claims, by a person of ordinary skill in the art without departing from the scope of the invention. For example, as noted earlier, any of a number of different methods could be used for background segmentation. The apparatus and methods of the present invention can be employed for diagnostic images obtained from any of number of different types of diagnostic imaging systems, including images obtained by scanning a photosensitive medium. While particularly well-suited to the diagnostic challenges posed by mammography, the method of the present invention can be applied in other diagnostic imaging applications wherein subtle, localized tissue density differences are diagnostically significant.

Thus, what is provided is an apparatus and method for enhancing a mammography image in order to provide consistent rendering for images obtained from one or more imaging systems connected to a network.

PARTS LIST

20. Image capture device
22. Image data
24. Image processing system
28. Archival system
30. Display
34, 36 Consistent rendering processor
40. Network
42. Imaging system
44. Imaging site
50. Consistency control module
52. Logic circuitry
54. Memory
56. Instructions
58. Network interface
80. Skin line threshold control point
82. Dense threshold control point
84. Dense region
86. Histogram
90. Dense region control point
S100. Initial step
S110. Transform step
S120. Control point identification step
S122. Breast segmentation step
S124. Histogram range identification step
S126. Peripheral correction step
S128. Skin line detection step
S130. Density determination step
S140. Mapping step
S150. Rendering step
S200. Acquisition step
S210. Segmentation step
S220. Skin line detection step
S230. Segmentation step
S240. Activity rate determination step
S250. LUT generation step
Al, Ar, $Ar_2$. Output values
Lp. Left point
Rp, $Rp_2$. Right point

The invention claimed is:

1. A method for rendering a mammography image, comprising:
obtaining mammography image data for a patient and storing the mammography image data in a computer-readable electronic memory;

generating a mapping that transforms the mammography image data to a predetermined output image data space to normalize the mammography image data for consistent rendering and display appearance in which each input data code value corresponds to an output image data value by:
- (a) estimating a relative amount of dense tissue from the mammography image data;
- (b) identifying at least a first control point that delineates breast tissue from non-tissue image content and a second control point that delineates a fatty tissue region from a dense tissue region;
- (c) allocating output image data values in the output image data space for the identified fatty and dense tissue content according to the estimated relative amount of dense tissue; and
- (d) mapping image data values to the allocated output image data values according to the first and second control points, wherein the mapping of the image data values to the allocated output image data values normalizes the mammography image data and provides consistent rendering and display appearance of the image data across a plurality of different displays; and rendering the mammography image data on a display according to the generated mapping.

2. The method of claim 1 wherein estimating the relative amount of dense tissue comprises obtaining a ratio that expresses percent density.

3. The method of claim 1 wherein generating a mapping forms a look-up table.

4. The method of claim 1 further comprising storing the generated mapping in a computer-accessible electronic storage medium.

5. The method of claim 4 wherein the mapping is stored in DICOM format.

6. The method of claim 1 wherein obtaining mammography image data comprises obtaining archived image data.

7. The method of claim 1 wherein allocating output image data values further comprises identifying a third control point that bounds or lies within the dense tissue region.

8. The method of claim 1 wherein estimating a relative amount of dense tissue comprises using a histogram analysis.

9. The method of claim 1 wherein the mammography image data is from a previously rendered image.

10. The method of claim 1 wherein the mammography image data is obtained from a digital radiography receiver.

11. The method of claim 1 wherein the mammography image data is obtained from a photosensitive medium.

12. The method of claim 1 wherein mapping image data values further comprises calculating spatial correlation for one or more pixels.

13. The method of claim 1 further comprising performing peripheral region density correction on the mammography image data.

14. The method of claim 1 wherein either or both first and second control points are predetermined.

15. The method of claim 1 wherein mapping image data values comprises using a linear relationship of input to output code values in either or both the fatty tissue region and the dense tissue region.

16. A method for rendering mammography image data comprising:

obtaining mammography image data for a patient and storing the mammography image data in a computer-readable electronic memory;

mapping the mammography image data to an output image data space to normalize the mammography image data for consistent rendering and display appearance, in which each data code value corresponds to an output image density by:
- (a) identifying at least a first control point that delineates tissue from background content, a second control point that delineates a fatty tissue region from a dense tissue region, and a third control point that lies within or bounds the dense tissue region;
- (b) estimating a relative amount of dense tissue within the mammography image data;
- (c) allocating the output image data space for identified fatty and dense tissue regions according to the relative amount of dense tissue estimated; and
- (d) generating a look-up table for mapping input image data values from the mammography image data to output values in the output image data space;

associating the generated look-up table with the mammography image data and storing the association, the look-up table, or both as DICOM data;

rendering the mammography image on a display according to the generated look-up table, wherein the mapping of the image data to the output image data space normalizes the mammography image data and provides consistent rendering and display appearance of the image data across a plurality of different displays.

17. The method of claim 16 wherein mapping the mammography image data further comprises performing a segmentation operation.

18. The method of claim 16 wherein the mammography image data is obtained from an image archival system.

19. The method of claim 16 wherein the mammography image data is obtained from a digital radiography receiver.

20. The method of claim 16 wherein the mammography image data is from a previously rendered image.

* * * * *